United States Patent [19]

Corvisier

[11] 4,327,715

[45] May 4, 1982

[54] DEVICE FOR FORMING COSTAL PROSTHESES

[76] Inventor: Pierre Corvisier, 133 Marechal Oudinot St., 54000 Nancy, France

[21] Appl. No.: 206,007

[22] Filed: Nov. 12, 1980

[30] Foreign Application Priority Data

Nov. 13, 1979 [FR] France ................................ 79 28157

[51] Int. Cl.³ .......................... A61F 5/04; A61B 17/18
[52] U.S. Cl. ....................................... 128/92 B; 3/1.9; 128/92 D; 128/92 G
[58] Field of Search ................. 128/92 B, 92 R, 92 D, 128/92 G, 89 R, 87 R, 83; 3/1.9

[56] References Cited

U.S. PATENT DOCUMENTS

| 2,486,303 | 10/1949 | Longfellow | 128/92 D |
| 2,502,902 | 4/1950 | Tofflemire | 128/92 R |
| 3,474,779 | 10/1969 | Wall | 128/89 R |

FOREIGN PATENT DOCUMENTS

| 2736972 | 3/1979 | Fed. Rep. of Germany . | |
| 2211851 | 7/1974 | France | 128/92 B |
| 2231352 | 12/1974 | France . | |
| 7616762 | 6/1976 | France . | |
| 7246276 | 7/1976 | France . | |
| 2353274 | 12/1977 | France | 128/92 B |

*Primary Examiner*—Ronald L. Frinks
*Attorney, Agent, or Firm*—Sandler & Greenblum

[57] ABSTRACT

The present invention relates to a device for forming costal prostheses, composed of elements of four types: (a) thin, narrow, straight elements, (b) bent elements having an angle of 15° to 45° comprising a pair of crimping jaws, (c) individual clips constituted by a pair of clamps opposite a pair of crimping jaws, (d) straight connecting members constituted by a pair of crimping jaws. The combination of these elements enables any necessary thoracic prosthesis to be composed.

3 Claims, 5 Drawing Figures

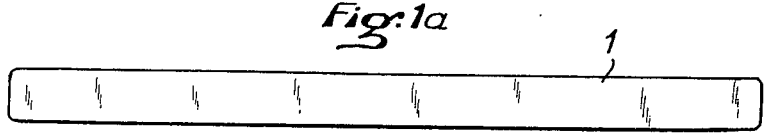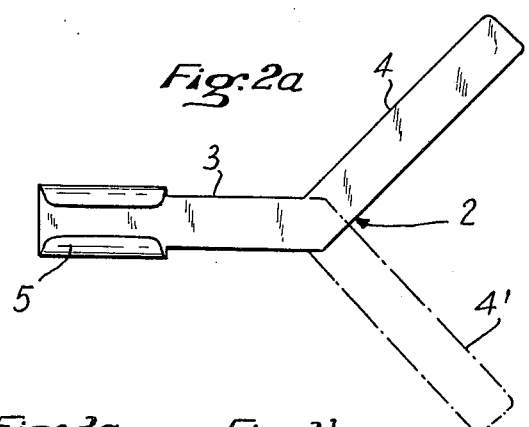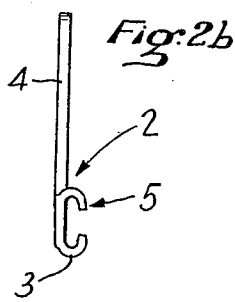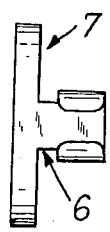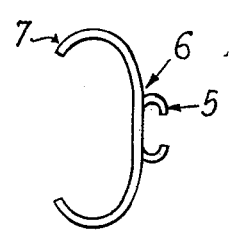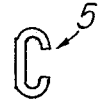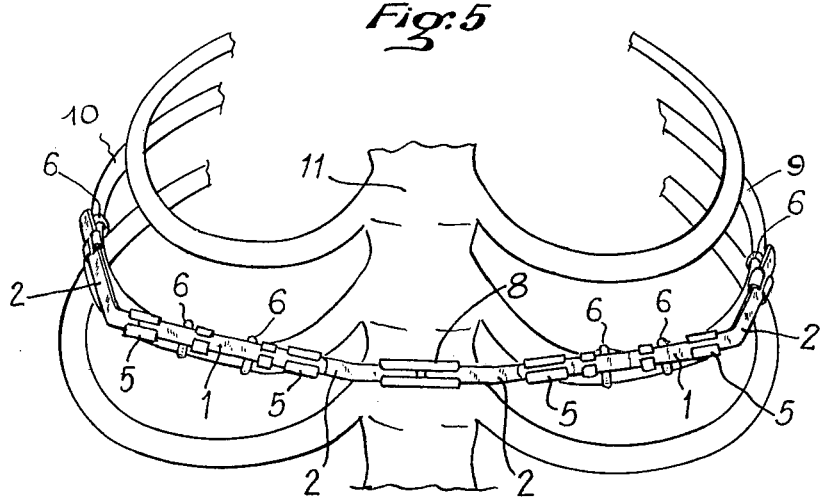

4,327,715

DEVICE FOR FORMING COSTAL PROSTHESES

BACKGROUND OF THE INVENTION

The present invention relates to a device composed of a plurality of individual parts especially designed to allow the formation of costal prostheses, by combination thereof when required, said prostheses being adapted to the shape of the thorax of any accident victim.

Whenever an accident victim has a fracture of one or more ribs, it is necessary, for the lungs to be protected and for them to be able to continue functioning, to reestablish the thoracic cage by restoring thereto a shape which is as close as possible to its natural shape.

To this end, it has already been proposed to use metallic elements made of suitable alloy.

French Pat. No. 72 46276 (2 211 851) discloses metal clips which are each composed of a small thin plate, of reduced length, provided with four pairs of claws which are distributed in two pairs of claws located respectively at the two opposite ends of said plate. These clips are designed to be placed on a fractured zone of a rib, two of the pairs of claws being closed on the rib on one side of the fracture and the other two pairs being closed on the other side of the same fracture.

In fact, these clips can only be used for localized fractures. Whenever there are several successive fractures of the same rib or when part of a rib is lost, or when there is considerable dislocation of the thoracic cage, the clips can no longer be used.

French Pat. No. 76 16762 (2 353 274) discloses a device designed to widen the possibilities of the claws of the first prior are mentioned hereinabove, which are limited to localized fractures. In this second prior art, use of a veritable rib splint is proposed; this splint in an elongated bar having at each of its two opposite end parts three pairs of claws integral with said bar; these claws may be closed on a rib on either side of a broken zone thereof; furthermore, individual clips are provided to be fixed to this bar in the median region located between the end pairs of claws.

It has appeared, on use, that an elongated bar provided with claws integral therewith does not enable the function of the thoracic cage, which has been badly injured as is frequently encountered in road accidents, to be reestablished.

Even by attempting to combine the clips comprising four pairs of claws of the first prior art mentioned above with the bars comprising six pairs of claws and the indivdual clips of the second prior art mentioned above, surgeons do not have at their disposal the means for reconstituting, easily and rapidly, a fractured thoracic cage which will enable it to function sufficiently well for the whole time taken for the bones to unite naturally, i.e. about 4 weeks.

It is an object of the invention to provide the necessary, sufficient means to enable surgeons to make a veritable thoracic prosthesis without difficulty, according to the morphology and needs of an accident victim, for all cases of serious accidents.

Whatever the extent and complexity of the thoracic prosthesis to be made, it is desirable that the means remain limited in number and that they be simple to manufacture and easy to use.

SUMMARY

According to the invention, this result is attained with the aid of a device comprising an assembly of elements which are of four different types only, adapted to be combined together to constitute any thoracic prosthesis.

These elements combine certain of the features of heretofore known clips and bars. The invention resides in the choice of the four types of elements, in the novel features of certain of them and in that these four types are necessary and sufficient for treating all accidents of the thorax.

A device according to the invention comprises:

(a) small thin, narrow, straight bars, (b) small thin, narrow, bent bars having a straight part and an inclined part making with the extension of the straight part an angle chosen between 15° and 45° in clockwise direction for one half and in anticlockwise direction for the other half of the bent bars, the straight part being provided at its end opposite the inclined part with a pair of crimping jaws adapted to receive and allow a straight bar or a bent bar to slide therebetween, and to be crimped thereafter on said bar to immobilize it, (c) individual clips comprising on one side a pair of crimping jaws and on the opposite side a pair of clamps which may be closed on a rib, (d) straight connecting members comprising a pair of crimping jaws adapted to receive and firmly connect straight bars in line with each other.

BRIEF DESCRIPTION OF THE DRAWINGS

In order to show the advantages of the invention more clearly, an embodiment by way of example will now be described with reference to the accompanying drawings, in which:

FIGS. 1a, 1b show a small straight bar in elevation and in side view, respectively.

FIGS. 2a, 2b show a small bent bar in elevation and in side view, respectively.

FIGS. 3a, 3b show an individual clip in elevation and in side view, respectively.

FIGS. 4a, 4b show a straight connecting member in elevation and in side view, respectively.

FIG. 5 is a schematic diagram explaining the mode of using the device according to the invention.

DESCRIPTION OF PREFERRED EMBODIMENTS

Referring now to the drawings, the following four elements form part of a thoracic prosthesis device according to the invention:

(a) small thin, narrow, straight bars 1 which may be of various lengths. The width is preferably 6 mm and the thickness 1.5 mm. Lengths may vary in increments of 30 mm for example, currently employed lengths being 40, 70, 100, 130, 160 mm for example.

(b) small thin, narrow, bent bars 2, of the same width and same thickness as the straight bars, comprising a straight part 3 and an inclined part 4 or 4'; the latter makes with the extension of the straight part 3 an angle chosen between 15° and 45°, either in anticlockwise direction as shown in solid lines at 4 on certain bars, or in clockwise direction as shown in dashed and dotted lines at 4' on certain other bent bars 2. The length of the straight part 3 and of the inclined part 4 or 4' is preferably 30 mm. On one of its main faces, the straight part 3 is provided in its end part opposite the inclined part 4, with a pair of crimping jaws 5. When open, the latter are sufficiently spaced apart to allow a small straight bar to slide easily therebetween. They are intended to be crimped thereafter on said bar in order to immobilize the straight bar and the bent bar firmly together. The angles of inclination are preferably chosen to range between 15° and 45° in increments of 10°.

(c) individual clips 6 which are each constituted by a pair of crimping jaws 5 as described hereinabove and by a pair of clamps 7 adapted to be closed on a rib, in manner known per se; it will be noted that the pair of jaws 5 and the pair of clamps 7 are directed in opposite directions but are not placed exactly back to back, but, on the contrary, they are offset in order not to be directly back to back.

(d) straight connecting members 8 which are essentially composed of a pair of crimping jaws 5 located on one side of a straight segment.

In all the elements which are provided therewith, the pairs of crimping jaws are sufficiently long to receive a small bar and to be crimped firmly thereon. In the straight connecting members 8, the length of the pair of crimping jaws is chosen so that two straight bars engaged end to end, in line with each other, in these jaws, are firmly connected after these jaws have been crimped.

For crimping the jaws 5, for closing the clamps 7 on the ribs and for their subsequent opening, suitable pliers already exist, which, as they are known, will not be described here.

To enable the usefulness of the device according to the invention to be appreciated and to show that it enables a result to be obtained which is unknown with the conventional means, FIG. 5 schematically shows, without exactitude due to the difficulty of illustrating it, the sternum 11 with two ribs 9, 10 on either side; these ribs are held together continuously from one side of the thorax to the other, firstly by a small bent bar 2 connected to rib 10 by a clip 6, then by a small straight bar 1 fixed to the bent bar 2 by jaws 5. This straight bar 1 is connected to rib 10 by clips 6. Then another bent bar 2 is fixed to the straight bar 1 by jaws 5, and a connecting member 8 enables it to be extended by another bent bar 2 followed by a straight bar 1 and finally a last bent bar 2. Clips 6 placed exactly at the desired spots ensure connection to the rib 9. The device according to the invention thus enables a veritable thoracic cage to be reconstituted, exactly as required, in order to maintain the broken ribs in place.

All the straight elements 1 and bent elements 2 are deformable in the sense of their thickness.

By the combination and curvature of the elements 1, 2, the desired prosthesis can always be formed directly on the accident victim, in a short time; when the clips 6 have been closed on the ribs, all the crimping jaws 5 are then crimped.

I claim:

1. In a device for forming a thoracic prosthesis comprising small bars and clips,
    elements of the following four types may be combined together to constitute, when required, any thoracic prosthesis:
    (a) small thin, narrow, straight bars,
    (b) small thin, narrow, bent bars having a straight part and an inclined part making with the extension of the straight part an angle chosen between 15° and 45° in clockwise direction for one half and in anti-clockwise direction for the other half of the bent bars, the straight part being provided at its end opposite the inclined part with a pair of crimping jaws adapted to receive and allow a straight bar to a bent bar to slide therebetween, and to be crimped thereafter on said bar to immobilize it,
    (c) individual clips comprising on one side a pair of crimping jaws and on the opposite side a pair of clamps which may be closed on a rib,
    (d) straight connecting members comprising a pair of crimping jaws adapted to receive and firmly connect straight bars in line with each other.

2. The device of claim 1, wherein the small bent bars comprising a straight part and an inclined part have angles of inclination ranging from 15° and 45° in increments of 10°.

3. The device of claim 1, wherein the pair of crimping jaws and the pair of clamps provided in the individual clips are offset in order not to be directly back to back.

* * * * *